US009840689B2

(12) United States Patent
Chaussin (10) Patent No.: US 9,840,689 B2
(45) Date of Patent: Dec. 12, 2017

(54) CONTAINER FOR BIOPHARMACEUTICAL CONTENT

(71) Applicant: Sébastien Chaussin, Aubagne (FR)

(72) Inventor: Sébastien Chaussin, Aubagne (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 362 days.

(21) Appl. No.: 14/370,227

(22) PCT Filed: Jan. 4, 2013

(86) PCT No.: PCT/FR2013/050014
§ 371 (c)(1),
(2) Date: Jul. 2, 2014

(87) PCT Pub. No.: WO2013/102738
PCT Pub. Date: Jul. 11, 2013

(65) Prior Publication Data
US 2014/0366969 A1   Dec. 18, 2014

(30) Foreign Application Priority Data

Jan. 5, 2012 (FR) ..................... 12 50124

(51) Int. Cl.
*B65D 88/54* (2006.01)
*C12M 1/00* (2006.01)

(52) U.S. Cl.
CPC ............. *C12M 29/00* (2013.01); *B65D 88/54* (2013.01); *Y10T 29/49826* (2015.01); *Y10T 137/86348* (2015.04)

(58) Field of Classification Search
CPC ......... C12M 29/00; B65D 88/54; F16L 3/221; F16L 3/222; F16L 3/233; Y10T 137/86348

(Continued)

(56) References Cited

U.S. PATENT DOCUMENTS 1,981,973 A * 11/1934 Tinnerman ................ F16L 3/04
126/39 N
2,548,104 A * 4/1951 Frison .................. A01K 11/001
24/674

(Continued)

FOREIGN PATENT DOCUMENTS

CN   101541594 A   9/2009
CN   101977673 A   2/2011

(Continued)

OTHER PUBLICATIONS

English translation of Chinese Office Action, dated Jun. 20, 2016, from corresponding Chinese Patent Application No. 201380004931.2.

(Continued)

*Primary Examiner* — Craig Schneider
*Assistant Examiner* — Nicole Gardner
(74) *Attorney, Agent, or Firm* — Young & Thompson (57) ABSTRACT

A container (10) for receiving biopharmaceutical content (C) in liquid, fluid or gaseous form, includes a peripheral wall (12) that is closed on itself, at least one transfer pipe (22), at least one guiding element (30; 130), and wherein the at least one guiding element (30; 130) includes a gripping member (32; 132) and an attachment member (44; 144). The gripping member (32; 132) and the attachment member (44; 144) are structurally separate and independent of one another and the guiding element (30; 130) has reciprocal assembly elements (60; 160) allowing the structural or functional assembly of the gripping member (32; 132) with the attachment member (44; 144) to ensure the positioning of the gripping member (32; 132) close to the attachment member (44; 144) and the connecting area (46; 146) of the corresponding peripheral wall (12).

14 Claims, 5 Drawing Sheets

(58) Field of Classification Search
USPC .................................. 137/590; 248/65–74.5
See application file for complete search history.

(56) References Cited

U.S. PATENT DOCUMENTS

| | | | | |
|---|---|---|---|---|
| 2,937,834 | A * | 5/1960 | Orenick | F16L 3/14 174/40 CC |
| 3,552,696 | A * | 1/1971 | Orenick | F16L 3/233 248/71 |
| 4,209,259 | A * | 6/1980 | Rains | B01F 13/0827 366/273 |
| 4,445,630 | A * | 5/1984 | Gartman | B60P 3/224 137/587 |
| 4,568,215 | A * | 2/1986 | Nelson | B29C 65/0672 24/297 |
| 4,766,651 | A * | 8/1988 | Kobayashi | B60R 16/0215 24/16 PB |
| 4,875,647 | A * | 10/1989 | Takagi | F16L 3/233 24/16 PB |
| 4,919,373 | A * | 4/1990 | Caveney | F16B 2/08 24/16 PB |
| 5,362,642 | A | 11/1994 | Kern | |
| 5,443,232 | A * | 8/1995 | Kesinger | H02G 3/263 248/62 |
| 5,921,510 | A * | 7/1999 | Benoit | F16L 3/2334 248/68.1 |
| 5,926,921 | A * | 7/1999 | Benoit | B65D 63/1072 24/16 PB |
| 6,006,678 | A * | 12/1999 | Merit | A47F 5/005 108/60 |
| 6,105,908 | A * | 8/2000 | Kraus | F16L 3/137 24/16 PB |
| 6,367,745 | B1 | 4/2002 | Winton, III | |
| 6,550,723 | B2 * | 4/2003 | Fraley, II | F16L 3/233 248/70 |
| 6,854,693 | B2 * | 2/2005 | Harrison | H02G 3/32 24/16 PB |
| 7,055,783 | B2 * | 6/2006 | Rosemann | B60R 16/0215 24/297 |
| 7,753,321 | B2 * | 7/2010 | Geiger | B60R 16/0215 248/68.1 |
| 8,028,962 | B2 | 10/2011 | Geiger | |
| 8,579,240 | B2 * | 11/2013 | Germ | H02G 3/263 24/16 PB |
| 8,690,129 | B2 * | 4/2014 | Ludwig | B01F 3/04269 261/121.1 |
| 9,044,718 | B2 * | 6/2015 | Ludwig | B01F 3/04269 |
| 9,074,171 | B2 * | 7/2015 | Gueneron | C12M 23/26 |
| 9,329,163 | B2 * | 5/2016 | Chaussin | G01N 33/48 |
| 2001/0054671 | A1 * | 12/2001 | Kondo | F16L 3/1025 248/74.3 |
| 2002/0000499 | A1 * | 1/2002 | Aoki | F16L 3/10 248/74.4 |
| 2002/0063189 | A1 * | 5/2002 | Coudrais | F16L 3/13 248/68.1 |
| 2002/0079409 | A1 * | 6/2002 | Fraley, II | F16L 3/233 248/74.3 |
| 2005/0139732 | A1 * | 6/2005 | Kato | B60R 16/0207 248/71 |
| 2006/0270036 | A1 * | 11/2006 | Goodwin | B01F 3/04269 435/395 |
| 2008/0217188 | A1 * | 9/2008 | Borchert | B29C 47/0023 206/0.6 |
| 2010/0116366 | A1 * | 5/2010 | Gattozzi | B29C 49/20 137/587 |
| 2010/0186197 | A1 | 7/2010 | Inomata et al. | |
| 2011/0013473 | A1 * | 1/2011 | Ludwig | B01F 3/04269 366/101 |
| 2011/0013474 | A1 * | 1/2011 | Ludwig | B01F 3/04269 366/102 |
| 2011/0038222 | A1 * | 2/2011 | Ludwig | B01F 3/04269 366/102 |
| 2012/0003733 | A1 * | 1/2012 | Gueneron | C12M 23/26 435/289.1 |
| 2014/0209194 | A1 * | 7/2014 | Thirlaway | B60K 15/03 137/590 |
| 2014/0238515 | A1 * | 8/2014 | Thirlaway | B60K 15/03 137/576 |
| 2014/0366969 | A1 * | 12/2014 | Chaussin | C12M 29/00 137/590 |
| 2016/0053920 | A1 * | 2/2016 | Walton | F16M 13/027 248/68.1 |

FOREIGN PATENT DOCUMENTS

| | | |
|---|---|---|
| WO | 2009/116002 | 9/2009 |
| WO | 2010/106282 | 9/2010 |

OTHER PUBLICATIONS

English translation of Chinese Office Action, dated Jul. 23, 2015, from corresponding Chinese Patent Application No. 201380004931.2.

International Search Report dated May 7, 2013, corresponding to PCT/FR2013/050014.

* cited by examiner

CONTAINER FOR BIOPHARMACEUTICAL CONTENT

The invention relates to the technical field of containers for receiving biopharmaceutical content(s).

It relates more particularly to the field of containers for receiving biopharmaceutical content and comprising at least one transfer pipe for carrying transfer products as well as one or more guiding element(s) supported by the container and intended for maintaining the transfer pipe in position relative to the peripheral wall of the container.

In this technical field, there are various known prior art solutions responding to the issues with maintaining transfer pipes in position relative to the container.

In particular, a container according to the preamble of claim 1 is known to persons skilled in the art by the example given in patent WO-A1-2010106282. That patent describes a mixing container comprising a flexible container adapted to receive biopharmaceutical content, means for mixing the biopharmaceutical content, and aeration means formed in part by a tubular member extending to air distribution means located inside the container. In addition, the tubular member is held in position in the container by means of guiding elements attached to the peripheral wall by bonding, welding, etc. These guiding elements may be implemented from adhesive strips, straps, or clamps arranged at various places along the tubular aeration member.

However, such an embodiment has several disadvantages. First, placing the transfer pipes inside the guiding elements—once these elements are in position against the peripheral wall—is not easy because the guiding elements are often difficult to access inside the container. It may therefore be necessary to enter the container in order to associate the transfer pipes with the guiding elements, which is not ergonomic and creates contamination issues. Moreover, the placement of the transfer pipes in the guiding elements can be tricky and involves heavy and repeated stresses on the peripheral wall of the container, which may cause blemishes in its appearance or even structural defects affecting its fluid-tightness. Given these issues, it is possible for the transfer pipes to be positioned incorrectly, causing difficulties when the containers are used. In addition, the problems encountered by operators when placing the transfer pipes in the guiding elements slows their productivity during container production.

WO-A1-2009116002 relates to a container similar to the one presented above and therefore has the same disadvantages and limitations.

Also known from the prior art is the line of CultiBag STR® products marketed by the applicant, which is another form of container for receiving biopharmaceutical content. This CultiBag STR® container comprises a peripheral wall consisting of plastic films welded to one another so as to define an inner chamber for receiving biopharmaceutical content. It also comprises transfer pipes for carrying transfer products, and guide loops to guide these transfer pipes inside the container. More particularly, the guide loops are formed by strips of plastic material whose two ends are sandwiched within the weld areas of the plastic films forming the peripheral wall of the container. The transfer pipes can thus be passed through the guide loops to ensure their positioning close to the weld areas of the peripheral wall.

Such an embodiment has disadvantages, however. First, the placement of the transfer pipes within the guide loops is tricky, and even more so since the position of the guide loops is determined by the position of the weld areas of the peripheral wall of the container. Actual access to these guide loops may therefore be difficult. As before, the placement of the transfer pipes in the guide loops applies heavy and repeated stresses on the weld areas of the container, which can cause leaks. In addition, such an embodiment requires the use of guide loops sufficiently wide to allow the transfer pipes to pass through. As a result, the guiding of these transfer pipes in the inner receiving chamber is imprecise and may result in excessive strain on the guide loops or excessively loose areas. It is therefore impossible to guarantee an exact position of the transfer pipes or of the areas for introducing and removing the transfer product. In addition, the attachment of the guide loops between the plastic films of the peripheral wall of the container requires the use of specific and complex weld parameters, which can cause difficulties in the production process and requires special vigilance concerning manufacturing defects.

A container for receiving biopharmaceutical content is known from U.S. Pat. No. 5,362,642, comprising a peripheral wall as well as transfer pipes for the introduction and/or removal of transfer products. However, in this case, the transfer pipes are not held against the wall of the container and their position is only imposed by gravity, which causes them to lie partially vertically.

Such an embodiment therefore does not ensure a precise positioning of the transfer pipes, as they do not follow a predetermined path. It is therefore impossible to introduce or extract the transfer product(s) at predetermined locations.

In a completely different technical field concerning the support and guidance of electrical wires, there is known prior art from U.S. Pat. No. 8,028,962. This patent discloses an attachment assembly for securely holding electrical wires on a supporting element. More particularly, the attachment assembly comprises a loop connected to a mounting stud which can be secured in a hole of the supporting element. The attachment assembly further comprises an adjustable tie intended to be first introduced into the loop and then tightened around the electrical wires to hold them in place.

Also known in this different technical field of maintaining electrical wires, is U.S. Pat. No. 6,367,745 which describes an attachment assembly comprising a loop attached to a mounting base. The mounting base is force fitted from the back into a sheet panel. The attachment assembly comprises a tie intended to be first introduced into the loop and then tightened around the electrical wires to hold them in place.

Such embodiments, in addition to their belonging to a technical field that is vastly different from that of the invention, therefore do not allow simple placement of the electrical wires when the attachment assembly is positioned in a location that is difficult to access.

In this context, the aim of the present invention is to propose a container for receiving biopharmaceutical products that is without at least one of the limitations mentioned above.

To this end, a first aspect of the invention relates to a container for receiving biopharmaceutical content in liquid, fluid, or gaseous form, comprising a peripheral wall that is closed on itself and that defines an inner receiving chamber able to receive biopharmaceutical content; at least one transfer pipe having a proximal end portion that opens to the inner receiving chamber and a distal end portion that opens to the outside of the container, to allow carrying a transfer product between said inner receiving chamber and the outside of said container; at least one guiding element able to be supported by the peripheral wall and to maintain the at least one transfer pipe in position close to said peripheral wall so as to impose a predetermined path between the proximal end portion and the distal end portion. The at least one guiding element comprises a gripping member able to be structurally secured to said at least one transfer pipe, and an attachment member able to be attached to any predetermined connection area of the peripheral wall without affecting its fluid-tightness. The invention is further characterized in that the gripping member and the attachment member are structurally separate and independent of one another and in that the guiding element has reciprocal assembly means allowing the structural or functional assembly of the gripping member, when the latter is secured to the at least one transfer pipe, with the attachment member, when the latter is attached to the connection area, to ensure the positioning of said gripping member close to said attachment member and close to the connection area of the corresponding peripheral wall.

With this arrangement, it is possible to facilitate the proper placement of the transfer pipes in the inner receiving chamber, since the operator can first clamp the transfer pipe(s) with the gripping member and attach the attachment member against the peripheral wall, and then can carry out the simplified assembly of the gripping member and attachment member. The risks of contaminating the inner receiving space or causing structural or visual defects during the assembly operation are thus greatly reduced. In addition, being able to use the gripping member prior to its association with the attachment member provides effective clamping of the transfer pipes, reduces the likelihood of improper positioning, and thus ensures a higher degree of precision. Similarly, being able to secure the attachment member to the peripheral wall of the container prior to its association with the gripping member and transfer pipes simplifies, facilitates, and accelerates this step in the production process.

In one embodiment, the attachment member has a mounting base provided with sufficient inherent resistance to prevent any structural deformation in the absence of external stresses. Unlike flexible straps which are difficult to weld or bond on the peripheral wall of the container, the use of a mounting base having inherent resistance allows the possibility of securing this mounting base against the peripheral wall under preferred conditions.

In this case, according to a first embodiment, the mounting base has a flat face adapted for attachment to one of the connection areas of the peripheral wall by an irreversible attachment method such as welding, gluing, or a similar method.

In this case, according to a second embodiment, the mounting base and a reciprocal assembly means are adapted to be positioned on each side of the peripheral wall so as to sandwich one of the connection areas of the peripheral wall between them and maintain the attachment member in position on said connection area.

More particularly, according to a first variant embodiment, the mounting base and the reciprocal assembly means have complementary geometric profiles which can be mechanically assembled together, reversibly or irreversibly, without passing through the peripheral wall or altering the structural continuity of said wall. Such an embodiment avoids having to perform a welding or bonding operation, while holding the attachment member in position in a precise and adjustable manner.

Conversely, according to a second variant embodiment, the peripheral wall has at least one attachment opening, with one or the other of the mounting base and the reciprocal assembly means being adapted to be attached around the attachment opening in a manner that maintains the fluid-tightness of the inner receiving space defined by the peripheral wall, one or the other of said mounting base and said reciprocal assembly means being adapted to pass through the attachment opening, the mounting base and the reciprocal assembly means having complementary geometric profiles which can be mechanically assembled together, reversibly or irreversibly. This second variant is also advantageous because it provides an effective assembly of the mounting base with the reciprocal assembly means, as these two parts can come into direct structural contact with one another.

In one embodiment, the gripping member is formed by encircling means adapted to grip a coupling portion of at least one transfer pipe. This provides an adjustable, precise gripping member that can be used to grip one or more transfer pipe(s) while limiting the risk that they will be crushed.

In this case, according to one embodiment, the encircling means have clamping means able to grip the at least one transfer pipe by adjusting to its dimensions, as well as locking means able to lock the clamping means in the clamped position, once the encircling means are adjusted to the dimensions of the at least one transfer pipe, without crushing or bending said pipe due to the clamping force. Such an embodiment is particularly effective for obtaining a precise grip that is easily adapted to the shapes of the gripped pipes(s).

In this case, in an additional or alternative embodiment, the encircling means have an elasticity enabling them to clamp the at least one transfer pipe without crushing or bending said pipe due to the clamping force. It is thus possible to increase the clamping force while limiting the risk that crushing will occur.

According to a first embodiment, a portion of the reciprocal assembly means is formed on the gripping member, and the complementary portion on the attachment member, so as to provide a direct mechanical connection between said gripping member and said attachment member. This reduces the number of parts used, and simplifies the manufacturing and assembly of the guiding element.

According to a second alternative embodiment, the reciprocal assembly means comprise an intermediate connection member that is distinct from said gripping member and said attachment member. It is thus possible to use a very simple gripping member—for example a locking ring—while using an intermediate connection member to cooperate in a more complex manner with the attachment member, in order to simplify their assembly.

In one embodiment of this, the intermediate connection member comprises means for securing to the attachment member that are adapted to establish a mechanical connection between the intermediate connection member and the attachment member, said mechanical connection being chosen from among a solid coupling which has the advantage of being simple to implement, a ball and socket coupling or a universal coupling which provides some flexibility in the position and orientation of the gripping member and transfer pipe(s), and a pivoting coupling which facilitates the positioning of the gripping member and transfer pipe(s), particularly if the orientation of the latter causes placement problems.

Assuming the use of the intermediate connection member, in one variant, one among the intermediate connection member and the attachment member forms a male element and the other forms a female element, one among the male and female elements having a flexibility allowing the mechanical connection of the attachment member to the intermediate connection member by forcibly snapping said male element into said female element. It is thus particularly quick and easy to complete the functional assembly of the gripping member with the attachment member.

Still assuming the use of the intermediate connection member, in another variant, the intermediate member comprises means for securing to the gripping member.

In this case, the means for securing to the gripping member are formed by at least one loop integral to the intermediate connection member and through which the gripping member can pass. Such an embodiment is particularly simple to implement, especially for the gripping of the transfer pipe(s).

Assuming the use of the intermediate connection member, in another variant, said member has a receiving cradle adapted to match the shape of the coupling portion of the at least one transfer pipe when the latter is clamped by the gripping member. It is thus possible to increase the clamping forces on the transfer pipe(s) to ensure its (their) positioning while limiting the risk that said transfer pipe(s) will be crushed.

In one embodiment, the at least one guiding element is attached to the inner face or the outer face of the peripheral wall. It may be advantageous to provide guidance for one or more transfer pipe(s) on the outer face of the peripheral wall of the container.

In one embodiment, the container comprises n transfer pipes, n being an integer greater than 1, and at least one spacer having m receiving seats, m being an integer greater than 1, adapted to receive the n transfer pipes and prevent said n transfer pipes from coming in contact with each other. By thus preventing the transfer pipes from coming in contact with each other, it is possible to reduce the risk of the pipes being crushed.

In this case, according to one embodiment, the m receiving seats are regularly distributed along the perimeter of the spacer so as to evenly distribute the clamping forces applied to the n transfer pipes when said pipes are in the receiving seats. Similarly, such an arrangement limits the concentration of clamping forces on a coupling portion of one of the transfer pipes and therefore reduces the risk of these transfer pipes being crushed.

In one embodiment, a first guiding element is supported by a first connection area of the peripheral wall and retains the proximal end portion of a first transfer pipe so that said pipe is guided to a first location corresponding to the area for the introduction or removal of a first transfer product. In this manner it is possible to remove or introduce the transfer product at a precise location on the container, and therefore to substantially improve the parameters of the reaction occurring within the inner receiving space of the container.

In this case, according to one embodiment, the container comprises a second guiding element distinct from the first guiding element, supported by a second connection area of the peripheral wall and retaining the proximal end portion of a second transfer pipe so that said pipe is guided to a second location different from the first location and corresponding to the area for the introduction or removal of a second transfer product. It is then possible to generate more efficient reactions which take into account the location where multiple transfer products are introduced or removed.

A second aspect of the invention relates to a method for producing a container for receiving biopharmaceutical content in liquid, fluid, or gaseous form, according to the first aspect of the invention, characterized in that it comprises a series of steps consisting of having a peripheral wall intended to be closed on itself in order to define an inner receiving chamber capable of receiving biopharmaceutical content; structurally securing at least one transfer pipe having a proximal end portion and a distal end portion, to a gripping member; attaching an attachment member that is structurally separate and independent of the gripping member, to any predetermined connection area of the wall without impacting its fluid-tightness; then structurally or functionally assembling said gripping member with said attachment member in order to form a guiding element that ensures the positioning, of said gripping member and of the at least one transfer pipe it secures, close to said attachment member and close to the connection area of the corresponding peripheral wall.

In this case, according to a first variant embodiment, the attachment member has a mounting base provided with a flat face which is attached to one of the connection areas of the peripheral wall by an irreversible attachment method such as welding, gluing, or a similar method.

In this case, according to a second variant embodiment, the attachment member has a mounting base and a reciprocal assembly means which are positioned on each side of the peripheral wall and are mechanically assembled together, reversibly or irreversibly, without passing through the peripheral wall or altering the structural continuity of said wall, so as to enclose one of the connection areas of the peripheral wall and maintain the attachment member in position on said connection area.

Thus, according to one embodiment, the peripheral wall has at least one attachment opening and the attachment member has a mounting base and a reciprocal assembly means, with one or the other of the mounting base and the reciprocal assembly means being secured around the attachment opening in a manner that maintains the fluid-tightness of the inner receiving space defined by the peripheral wall, one or the other of said mounting base and said reciprocal assembly means being positioned so as to pass through the attachment opening, the mounting base and the reciprocal assembly means being mechanically assembled to one another, reversibly or irreversibly, so as to sandwich one of the connection areas of the peripheral wall and hold the attachment member in position on said connection area.

In one embodiment, the gripping member is structurally secured to the at least one transfer pipe by the grip of encircling means against a coupling portion of said at least one transfer pipe.

In one embodiment, the gripping member and the attachment member are connected to one another by a direct mechanical connection.

In one embodiment, prior to assembly of the gripping member with the attachment member, an intermediate connection member that is distinct from said gripping member and from said attachment member is secured to the gripping member; said intermediate connection member is then secured to the attachment member to ensure the positioning, of said gripping member and of the at least one transfer pipe it secures, close to said attachment member and close to the connection area of the corresponding peripheral wall.

In one embodiment, prior to structurally securing n transfer pipes, n being an integer greater than 1, with the gripping member, said n transfer pipes are placed in receiving seats formed on a spacer so as to prevent said n transfer pipes from coming in contact with each other and to prevent any of said n transfer pipes from being crushed by the clamping force.

In one embodiment, a first set of gripping members is secured to a first set of coupling portions arranged along a first set of transfer pipe(s); a first set of attachment members, structurally separate and independent of the gripping members, is attached to a first set of connection areas of the peripheral wall without impacting its fluid-tightness; then each gripping member of the first set is structurally or functionally assembled to an attachment member of the first set in order to guide the first set of transfer pipe(s) close to the peripheral wall and all the way to a first location corresponding to the area for the introduction or removal of a first transfer product.

In this case, according to a first variant embodiment, the gripping members of the first set are secured along the first set of transfer pipe(s) so as to define predetermined securing intervals between the coupling portions of the first set; the attachment members of the first set are attached to the peripheral wall so as to define predetermined connection intervals that are similar to the securing intervals, between the connection areas of the first set; such that, after the structural or functional assembly of the gripping members and attachment members of the first set, the first set of transfer pipe(s) defines a first path coinciding with the path defined by the first set of connection areas on the peripheral wall.

In this case, according to a first variant embodiment, the gripping members of the first set are secured along the first set of transfer pipe(s) so as to define predetermined securing intervals between the coupling portions of the first set; the attachment members of the first set are attached to the peripheral wall so as to define predetermined connection intervals that are smaller than the securing intervals, between the connection areas of the first set; such that, after the structural or functional assembly of the gripping members and attachment members of the first set, the first set of transfer pipe(s) defines a first path distinct from the path defined by the first set of connection areas on the peripheral wall. This variant allows precisely defining the path of the first set of transfer pipe(s) while limiting the number of guiding elements to be used.

According to one embodiment, a second set of gripping members are secured along one or more other transfer pipe(s); a second set of attachment members, structurally separate and independent of the gripping members, are attached to a second set of connection areas of the peripheral wall without impacting its structural continuity or its fluid-tightness and defining a second predetermined path; then each gripping member of the second set is structurally or functionally assembled to an attachment member of said second set in order to guide the second set of transfer pipe(s) close to the peripheral wall and all the way to a second location corresponding to the area for the introduction or removal of a second transfer product.

Other features and advantages of the invention will become apparent from the description given below. This description is illustrative only and is not intended to be limiting, and refers to the accompanying drawings in which.

A container 10 according to the invention is described with reference to FIG. 1.

The container 10 in question is designed to receive biopharmaceutical content C for the purposes of packaging, mixing, carrying out a biological reaction, or for any other chemical reaction.

The biopharmaceutical content C can contain one or more components that may be in liquid or gas phase or solid phase such as powder. If necessary, the container 10 can contain cells, microorganisms, etc.

Figure 1:
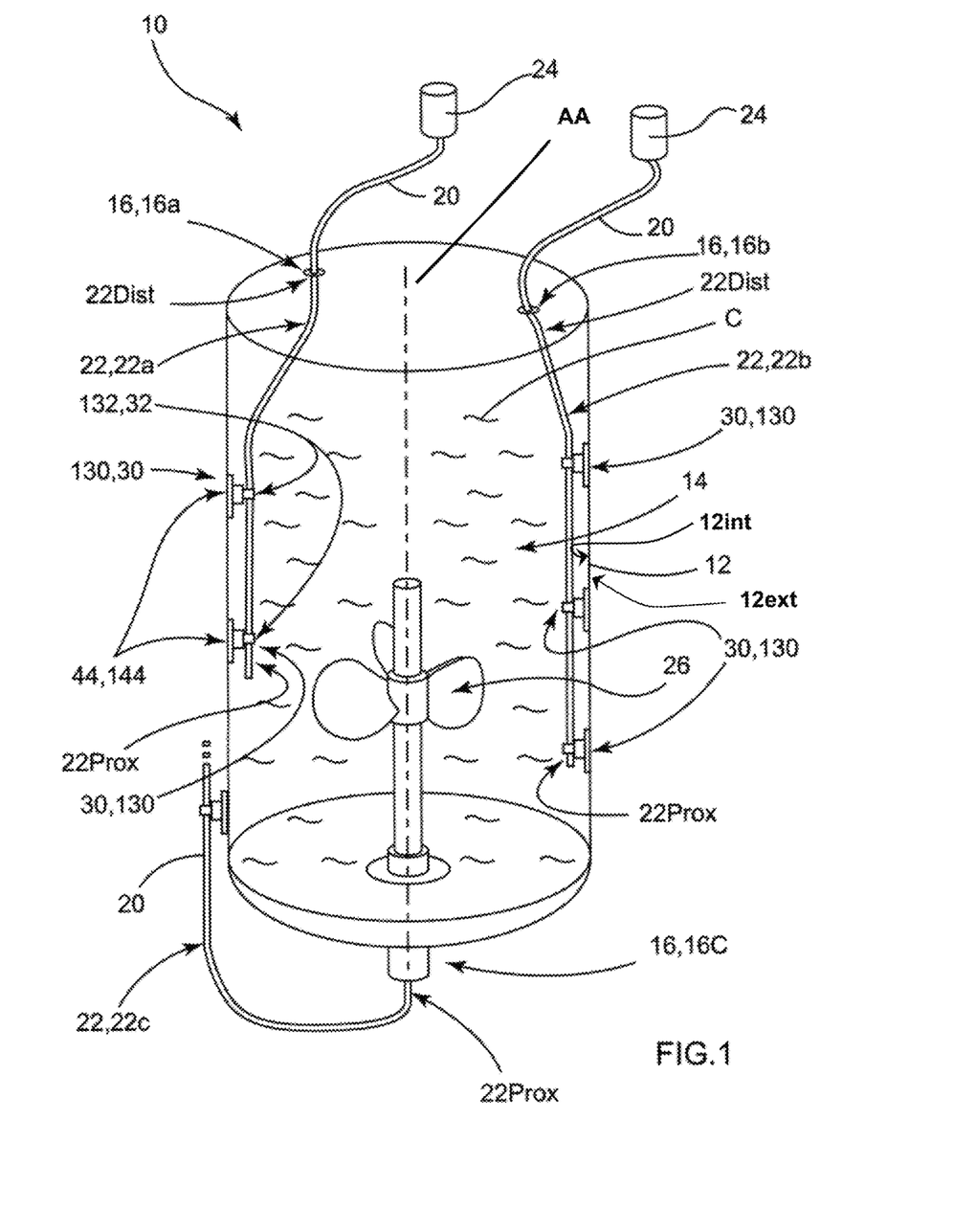
FIG. 1 is a general perspective view of a container according to the invention, comprising a peripheral wall defining an inner receiving space for the biopharmaceutical content, two transfer pipes, and several guiding elements attached to the inner face of the peripheral wall to guide the transfer pipes along two predetermined paths and to two separate locations within the inner receiving space.

The container 10 according to the embodiment of FIG. 1 has a cylindrical geometry of revolution around an axis AA that is vertically oriented when the container is in the usage position. However, it should be noted that the container 10 could have other shapes, including rectangular or some other shape.

The container 10 comprises, firstly, a peripheral wall 12 having an inner face $12_{INT}$ and an outer face $12_{EXT}$. This peripheral wall 12 may be formed from a single piece or from a plurality of pieces secured to each other by welding, gluing, or some other similar method that ensures a functional seal between the various pieces.

The peripheral wall 12 is closed on itself to form an inner receiving chamber 14 able to receive a certain amount of biopharmaceutical content C.

In one embodiment, the container 10 is disposable.

It can, in various variant embodiments, have a capacity ranging from 10 liters to 5000 liters depending on the requirements and applications.

In the following description, the container 10 is presented in the usage position, meaning in the position where it receives the biopharmaceutical content C. The words "vertical", "horizontal", "upper", and "lower" thus refer to the spatial positions of the elements when the container 10 is in a position that allows it to function. However, it is understood that the container 10 can occupy other positions or have other states, for example when it is in packaging or when it is not in operation.

The "axial" direction refers to that which is oriented at least substantially in the direction of axis AA, while the "radial" direction refers to that which is oriented in a direction substantially issuing from axis AA and extending in a plane perpendicular to said axis AA. A "transverse" plane is a plane substantially perpendicular to axis AA.

The terms "internal" or "inner", and "external" or "outer", respectively refer to that which is inside and outside the container 10.

The container 10 also includes at least one port 16 which cooperates with a hole provided in the peripheral wall 12 of the container 10 and which can be closed or open at any time to allow the introduction or removal of products generally considered as transfer products 20.

It should be noted that such a transfer product 20 can be any component that is or will be in the liquid, gas, or solid phase within the inner receiving space 14 of the container 10. Specifically, in some cases the transfer product 20 may correspond to the biopharmaceutical content C itself if introducing or removing it from the container 10. It could also correspond to reagents to be added to the container 10 in order to carry out the chemical reaction that will result in the formation of the biopharmaceutical content C, or conversely it may be a product of this chemical reaction that is to be removed from the container 10 in order to complete the formation of the biopharmaceutical content C. The transfer product 20 could also be a gas introduced into the container 10 in order to aerate the biopharmaceutical product C.

In the embodiment of FIG. 1, the container 10 comprises three separate ports 16.

As a non-limiting example, the first port can be an introduction port 16a for introducing one or more transfer product(s) 20—corresponding to reagents—from the outside into the inner receiving chamber 14. The second is an extraction port 16b for removing one or more transfer product(s) 20—corresponding to products of the chemical reaction—from the inner receiving chamber 14 to the outside. Lastly, the third is a drainage port 16c to allow completely emptying the container 10 of biopharmaceutical content C.

In this example, the introduction 16a and extraction 16b ports are placed at the upper end of the container 10 while the drainage port 16c is positioned at the lower end of the container 10.

Transfer pipes 22, intended for carrying transfer products between the inner receiving chamber 14 and the exterior of the container 10, may be associated with the ports 16 in fluid communication and with a fluid-tight and if necessary removable connection. Whether located outside the container 10 or within the inner receiving chamber 14, these transfer pipes 22 have a proximal end portion $22_{PROX}$ that opens to the inner receiving chamber 14 and a distal end portion $22_{DIST}$ that opens to the exterior of the container 10. These proximal $22_{PROX}$ and distal $22_{DIST}$ end portions, when connected to a port 16, are generally fluid-tight with and removable from said port. The distal end portion $22_{DIST}$ of the transfer pipe 22 may also be connected in a fluid-tight and generally removable connection with a tank 24, vessel, bag, or similar.

The container 10 thus has two transfer pipes 22 external to the container 10 and connecting two tanks 24 to the introduction 16a and extraction 16b ports.

The container 10 also comprises a transfer pipe 22, referred to as an introduction transfer pipe 22a, located within the inner receiving space 14 and connecting the introduction port 16a to an introduction point where the transfer product can be introduced.

The container 10 also comprises a transfer pipe 22, referred to as an extraction transfer pipe 22b, located within the inner receiving space 14 and connecting the extraction port 16b to an extraction point that is different from the introduction point, particularly in that they are not placed at the same height in the internal introduction space.

The container 10 further comprises a transfer pipe 22, referred to as a drainage transfer pipe 22c, located outside the container 10 and connecting the drainage port 16c to a drainage area (not shown).

It should be noted that the transfer product 20 to be introduced into the container 10 may be any kind of reagent, such as a biopharmaceutical product, a culture medium, biological cells, gas and particularly oxygen, etc. Similarly, the transfer product 20 to be extracted from the container 10 may correspond to the biopharmaceutical product C itself or to any other element located at a predetermined location within the container 10. The same is true for the transfer product 20 to be drained.

According to the embodiment in FIG. 1, the container 10 also comprises a mixing means 26 located within the inner receiving chamber 14 and capable of mixing the entire biopharmaceutical content C or only some of the components of this biopharmaceutical content C. It should be noted that it is also possible for the container 10 of the invention not to include such mixing means 26.

Said container 10 may include other components—such as sensors, heating system, cooling system, etc.—for improving the quality of the chemical reaction taking place within the inner receiving chamber 14 or, more simply, for packaging the biopharmaceutical content.

The container 10 also comprises at least one guiding element 30, 130.

More particularly, the container 10 illustrated in FIG. 1 comprises a first set of two guiding elements 30; 130.

These two guiding elements 30; 130 of the first set are supported by the inner face $12_{INT}$ of the peripheral wall 12 and maintain the introduction transfer pipe 22a close to this peripheral wall 12. The two guiding elements 30; 130 of the first set, which are located at different heights, thus impose a predetermined introduction path, vertical in this case, between the proximal $22_{PROX}$ and distal $22_{DIST}$ end portions of the introduction transfer pipe 22a.

One of the two guiding elements 30; 130 maintains the proximal end portion $22_{PROX}$ of the introduction transfer pipe 22a, guiding it to a predetermined location corresponding to the transfer product 20 introduction area.

With this arrangement, the transfer product 20 introduction area is precisely determined, which in turn can help to improve the parameters of the chemical reaction taking place within the inner receiving chamber 14 of the container 10.

The container 10 of FIG. 1 also comprises a second set of three guiding elements 30; 130.

These three guiding elements 30; 130 of the second set are supported by the inner face $12_{INT}$ of the peripheral wall 12 and maintain the removal transfer pipe 22b close to this peripheral wall 12. The three guiding elements 30; 130 of the second set, which are located at different heights, thus impose a predetermined introduction path, vertical in this case, between the proximal $22_{PROX}$ and distal $22_{DIST}$ end portions of the removal transfer pipe 22b.

One of the three guiding elements 30; 130 maintains the proximal end portion $22_{PROX}$ of the removal transfer pipe 22b, guiding it to a predetermined location corresponding to the transfer product 20 extraction area. The transfer product 20 extraction area, potentially different from the introduction area described above, is thus precisely determined as well.

The container of FIG. 1 further comprises a third set consisting of a single guiding element 30; 130.

This guiding element 30; 130 is attached to the outer face $12_{EXT}$ of the peripheral wall and maintains the drainage transfer pipe 22c outside the container 10 but close to its peripheral wall 12. This single guiding element 30; 130 imposes a predetermined drainage path between the proximal $22_{PROX}$ and distal $22_{DIST}$ end portions of the drainage transfer pipe 22c.

It should be noted that the paths imposed by the first and second sets of guiding elements 30, 130 are vertical here, but could be curved, angled, etc., depending on the requirements of the reaction and the space constraints within the inner receiving chamber 14.

Figure 2:
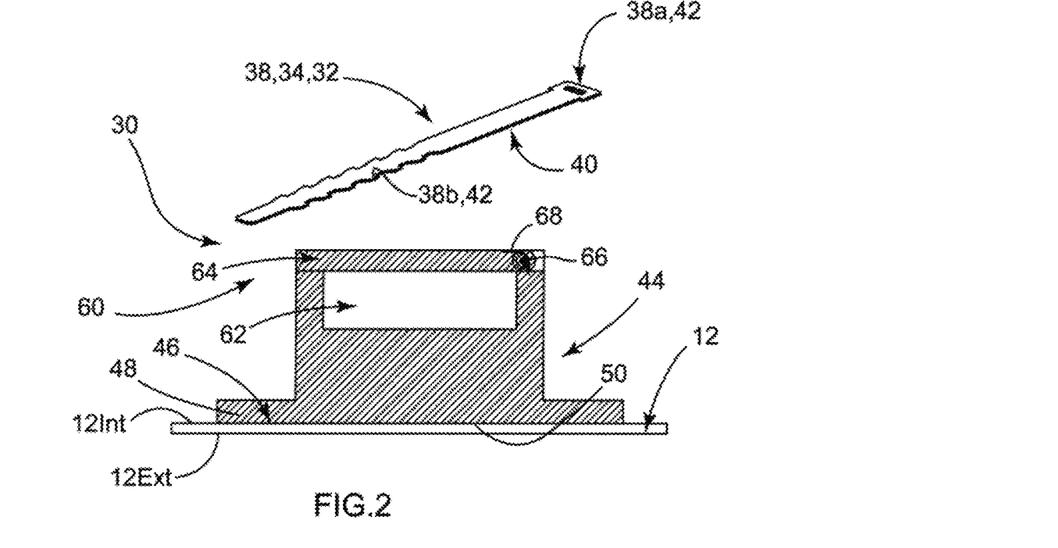
FIG. 2 is a detailed cross-sectional view of a first embodiment of a guiding element for the container according to the invention, where the guiding element is welded to the inner face of the peripheral wall and consists of a gripping member and an attachment member which are intended to be secured directly and structurally to each other.

A first exemplary embodiment of a guiding element 30 that could be used in the container 10 according to the invention is illustrated in FIG. 2.

Firstly, this guiding element 30 comprises a gripping member 32.

The gripping member 32 is able to be structurally or functionally secured to the transfer pipes 22.

More particularly, according to the embodiment of FIG. 2, this gripping member 32 forms encircling means 34 able to grip a coupling portion 36 of the transfer pipes 22.

The encircling means 34 therefore in this case resemble a strap 38 with one end having a loop 38a into which the other end can be inserted to form clamping means 40.

In order to encircle one or more transfer pipe(s) 22, it is possible to place the strap 38 around the coupling portion 36 of said transfer pipe(s) 22 and introduce the end of this strap 38 into the opposing loop 38a until the transfer pipe(s) 22 is (are) encircled. The encircling means 34 can thus be tight or slightly loose against the coupling portions 36 of the transfer pipes 22. However, they are retained in a manner that will not crush the coupling portions 36.

Such encircling means 34 have the advantage of adapting to the dimensions of the transfer pipe(s) 22 in order to clamp them all while managing the risk of crushing said one or more transfer pipe(s) 22.

The encircling means 34 also have a series of notches 38b distributed along the length of the strap 38 and able to cooperate with the loop 38a to form locking means 42 when the encircling means 34 are tightened around the coupling portions 36 of the transfer pipes 22.

Thus, when the clamping means 40 are adjusted against the coupling portion 36 of the transfer pipe(s) 22, the locking means 42 hold them in position and thus keep the encircling means 34 against said one or more transfer pipe(s) 22.

Alternatively, it should be noted that the encircling means 34 could also be formed from an enclosed loop (not shown) having sufficient elasticity to simultaneously constitute the clamping means 40 and the locking means 42. It is thus possible to stretch the loop to insert the transfer pipe(s) 22 and then allow its elasticity to tighten it around the coupling portion 36 of the transfer pipe(s) 22 and hold them in position, without the clamping force causing them to bend.

In other embodiments, the gripping member 32 can be implemented by any other means known to persons skilled in the art.

The guiding element 30 of FIG. 2 also comprises an attachment member 44.

This attachment member 44 is intended to be attached to any connection area 46 of the peripheral wall 12 without impacting its fluid-tightness.

More particularly, according to this embodiment, the attachment member 44 includes a mounting base 48 having sufficient inherent resistance to prevent structural distortion in the absence of external forces other than gravity. This inherent resistance allows easier handling of the mounting base 46 and facilitates its attachment to the connection area 46 of the peripheral wall 12. Conversely, the mounting base 46 could have a certain flexibility, to allow its attachment to any curved areas of the peripheral wall 12.

In the embodiment in FIG. 2, the mounting base 48 has a flat face 50 which can be secured directly to the peripheral wall 12, in particular by welding. Such a welded attachment has the advantage of being simple and does not require damaging the structural continuity of the peripheral wall 12. Alternatively, the attachment of the flat face 50 to the connection area 46 of the peripheral wall 12 could also be accomplished by gluing or by any other similar process offering advantages similar to welding.

According to the invention, the gripping member 32 and the attachment member 44 are structurally distinct and independent from one another.

The guiding element 30 has reciprocal assembly means 60.

These reciprocal assembly means 60 ensure the structural assembly of the gripping member 32, when the latter is secured to one or more transfer pipe(s) 22, with the attachment member 44, when the latter is attached to the connection area 46 of the peripheral wall 12.

Thus the assembly means 60 guarantee the positioning of the gripping member 32 close to the attachment member 44 and close to the connection area 46 of the corresponding peripheral wall 12.

According to the embodiment in FIG. 2, the reciprocal assembly means 60 are formed by an opening 62 provided in the body of the attachment member 44, which a closing flap 64 closes over.

More particularly, the closing flap 64 rotates about an axis 66 in order to move from an open position where the encircling means 34 are unrestrained, to a closed position where the closing flap 64 locks a portion of these encircling means 34 inside the opening 62. The closing flap 64 can then be retained in the closed position by a spring 68 as in the example of FIG. 2, or by other similar means.

In this manner, the strap 38 is locked within the opening 62 and the gripping member 32 remains in position close to the attachment member 44.

Such reciprocal assembly means 60 facilitate placement of the transfer pipes 22 inside the inner receiving chamber 14, since the operator can first clamp the transfer pipe(s) 22 with the gripping member 32 and place the attachment member 44 against the peripheral wall 12, and then assemble the gripping member 32 and attachment member 44. This reduces the risk of defects and of contamination in the inner receiving space 14 that could arise during the assembly operation. In addition, securing the gripping member 32 to the gripped pipe(s) 22 before its association with the attachment member 44 provides more precision and thus ensures proper positioning of the transfer pipe(s) 22 within the inner receiving chamber 14. Similarly, securing the attachment member 44 to the peripheral wall 12 of the container 10 prior to its association with the gripping member 32 and transfer pipe(s) simplifies and accelerates this step in the production process.

A second exemplary embodiment of a guiding element 130 that can be used in the container 10 according to the invention is illustrated in FIGS. 3, 4a, 4b, and 4c.

Figure 3:
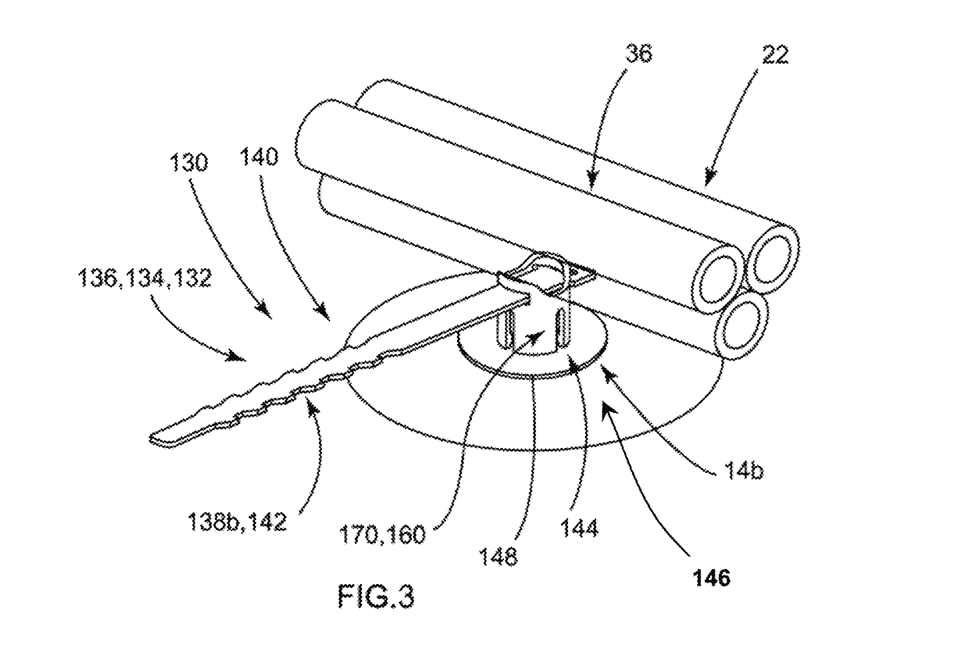
FIG. 3 is a detailed perspective view of a second embodiment of a guiding element for the container according to the invention, this guiding element receiving three transfer pipes and being composed of an attachment member, an intermediate connection member, and a gripping member consisting of a clamping and locking loop.
Figure 4A:
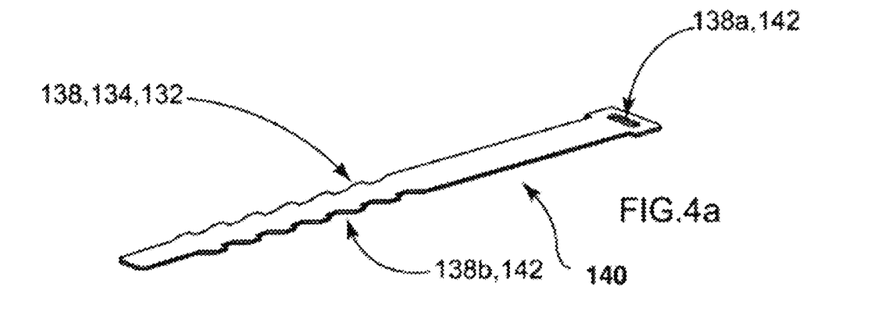
FIG. 4a is a detailed perspective view of the gripping member that is part of the guiding element of FIG. 3, where the gripping member is formed by a clamping and locking loop.
Figure 4B:
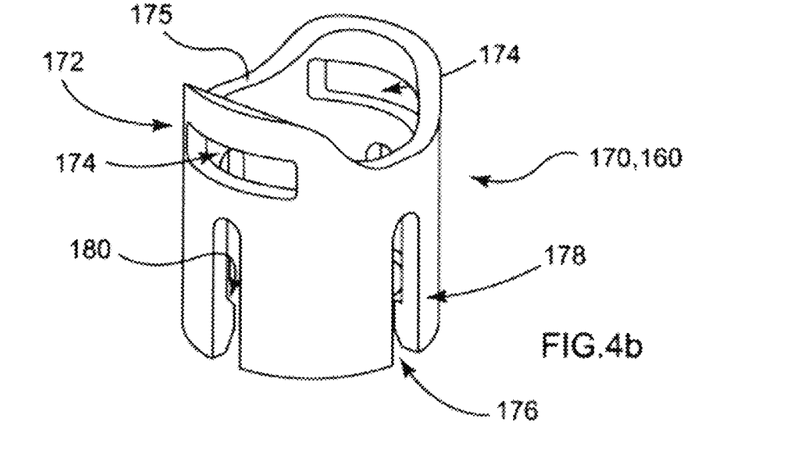
FIG. 4b is a detailed perspective view of the intermediate connection member that is part of the guiding element of FIG. 3, where this intermediate connection member comprises means for snap-on attachment to the attachment member.
Figure 4C:
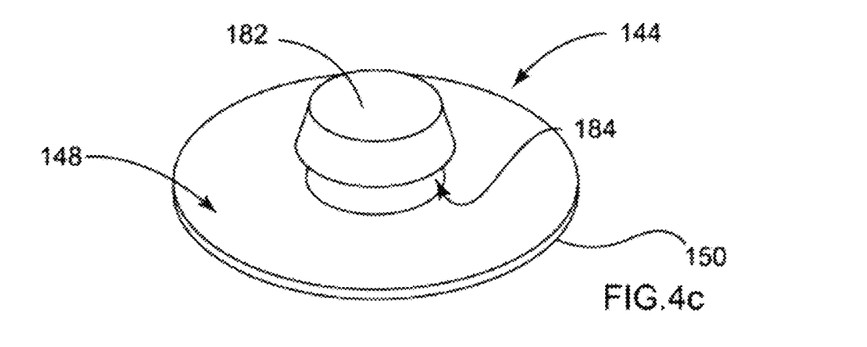
FIG. 4c is a detailed perspective view of the attachment member that is part of the guiding element of FIG. 3, where this attachment member comprises a mounting base provided with a flat face and having sufficient resistance to avoid structural deformation in the absence of external stresses.

This guiding element 130 comprises a gripping member 132 similar to the one in the embodiment in FIG. 2.

More particularly, the gripping member 132 can be secured structurally or functionally to the transfer pipes 22. It forms encircling means 134 that can be clamped around a coupling portion 136 of the transfer pipes 22.

The encircling means 134 resemble a strap 138 with one end having a loop 138a into which the other end can be inserted in order to form clamping means 140.

In order to clamp one or more transfer pipe(s) 22, it is possible to place the strap 138 around the coupling portion 136 of said transfer pipe(s) 22 and then introduce the end of this strap 138 into the opposing loop 138a until the transfer pipe(s) 22 is (are) clamped. The encircling means 134 can thus be tight or slightly loose against the coupling portions 136 of the transfer pipes 22. However, the pipes are held in a manner that will not crush the coupling portions 136 with the clamping forces.

The encircling means 134 also have a series of notches 138b distributed along the length of the strap 138 and able to cooperate with the loop 138a in order to form locking means 142 when the encircling means 134 are tightened into position around the coupling portions 136 of the transfer pipes 22.

Thus, when the clamping means 140 are adjusted against the coupling portion 136 of the transfer pipe(s) 22, the locking means 142 hold them in position and therefore retain the encircling means 134 against said one or more transfer pipe(s) 22.

As above, it is understood that the gripping member 132 could be based on an enclosed loop having sufficient elasticity to constitute the clamping means 140 and the locking means 142 simultaneously, or could be based on any other implementation.

The guiding element 130 of FIG. 3 also includes an attachment member 144.

This attachment member 144 is intended to be placed on and attached to any connection area 146 of the peripheral wall 12 without impacting its fluid-tightness.

More particularly, in this embodiment the attachment member 144 comprises a mounting base 148 having sufficient inherent resistance to avoid structural deformation in the absence of external stresses. This inherent resistance thus enables the mounting base 148 to be manipulated more easily and facilitates its attachment to the connection area 146 of the peripheral wall 12. Conversely, the mounting base 148 could have some flexibility, to allow attaching it to any curved areas of the peripheral wall 12.

The mounting base 148 has a flat face 150 which can be secured directly against the peripheral wall 12, in particular by welding. Such a welded attachment has the advantage of being simple and does not require damaging the structural continuity of the peripheral wall 12. However, the attachment of the flat face 150 against the connection area 146 of the peripheral wall 12 could also be achieved by gluing or by some other similar method.

According to the invention, the gripping member 132 and the attachment member 144 are structurally separate and independent from one another.

However, these gripping 132 and attachment 144 members are adapted to be functionally secured to each other by reciprocal assembly means 160 which ensure the functional assembly of the gripping member 132, when the latter is secured to one or more transfer pipe(s) 22, with the attachment member 144, when the latter is attached to the connection area 46 of the peripheral wall 12. Thus the reciprocal assembly means 160 guarantee the positioning of the gripping member 132 close to the attachment member 144 and close to the connection area 146 of the corresponding peripheral wall 12.

More particularly, according to the embodiment in FIG. 3, these reciprocal assembly means 160 are formed in part by an intermediate connection member 170 that is distinct from the gripping member 132 and the attachment member 144.

This intermediate connection member 170 has means 172 for securing it to the gripping member 132.

In particular, according to the embodiment in FIG. 3, the means 172 for securing to the gripping member 132 are formed by two loops 174 which the encircling means 134 can pass through before clamping the transfer pipe(s). Such means 172 for securing to the gripping member 132 offer the advantages of being simple to manufacture and simple to use.

In addition, these means 172 for securing to the gripping member 132 form, between the two loops 174, a receiving cradle 175 that matches the shape of at least one of the transfer pipe(s) 22. The receiving cradle 175 can thus receive said at least one transfer pipe(s) 22 to facilitate securing it to the intermediate connection member 170 while limiting the risk of crushing it.

The intermediate connection member 170 also has means 176 for securing to the attachment member 144.

More particularly, according to this embodiment, the intermediate member 170 for connecting to the attachment member 144 forms a female element 178 having a retaining projection 180 offering a certain flexibility due to the geometry of the intermediate connection member 170. The attachment member 144 forms a male element 182 having a complementary shoulder 184 which can be snapped into and retained by the female element 178.

In particular, the male element 182 can be forcibly introduced into the female element 178 by elastic deformation of the retaining projection 180, then pushed inside this female element 178 until the complementary shoulder 184 passes beyond the retaining projection 180. The retaining projection 180 then returns to its original shape and thus locks the complementary shoulder 184 inside the female element 178, at the same time locking the male element 182 inside said female element 178.

Such a mechanical connection has the effect of establishing a functional bond, quickly and with particular effectiveness, that secures the gripping member 132 to the attachment member 144. The possibility of contaminating the inner receiving chamber 14 during placement of the transfer pipe(s) 22 is greatly reduced as well. In addition, such a connection provides, between the intermediate connection member 170 and the attachment member 144, a pivoting coupling that facilitates the functional assembly of the gripping member 132 and attachment member 144, by not imposing a specific orientation of the gripping member 132—and therefore of the transfer tubes 22—relative to the attachment member 144. Lastly, it allows precise positioning of the transfer pipes 22 and thus ensures the introduction or removal of transfer products 20 at a predetermined location.

Of course, this mechanical connection and the reciprocal assembly means 160 could be implemented differently without departing from the scope of the invention. It would thus be possible to implement any other form of attachment by a solid coupling, a ball and socket coupling, a universal coupling, etc.

Figure 5A:
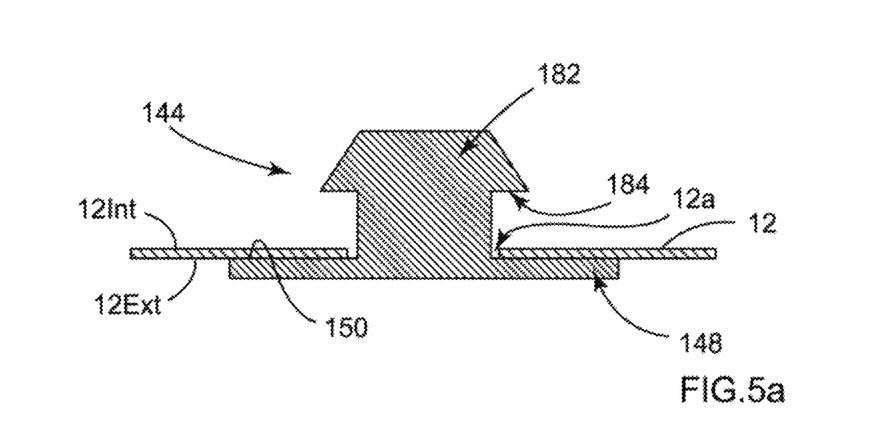
FIG. 5a is a detailed cross-sectional view of a first variant embodiment of a container according to the invention, in which the peripheral wall has an attachment opening and the attachment member is welded around the attachment opening, on the outer face of the peripheral wall, to ensure the fluid-tightness of this peripheral wall while allowing the assembly of said attachment member with the intermediate attachment member placed in the inner receiving space of the container.
Figure 5B:
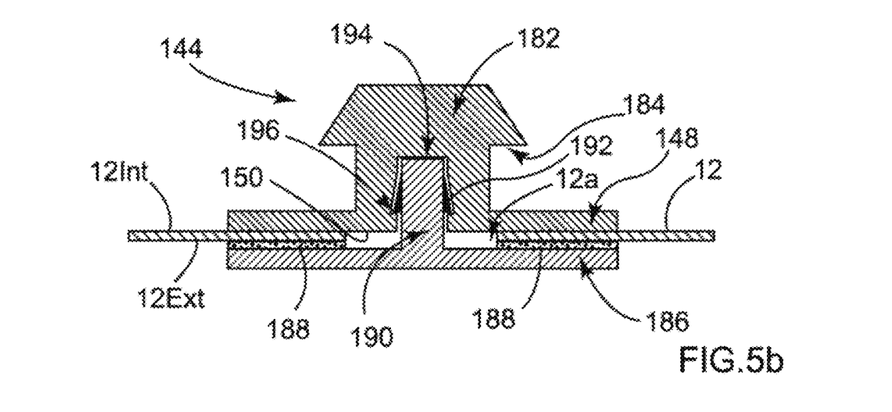
FIG. 5b is a detailed cross-sectional view of a second variant embodiment of a container according to the invention in which, firstly, the peripheral wall has a attachment opening, secondly, the attachment member is positioned against the inner face of the peripheral wall, and thirdly, a reciprocal assembly means is positioned against the outer face of the peripheral wall, around the attachment opening, so as to ensure the fluid-tightness of the peripheral wall while holding the attachment member in position.
Figure 5C:
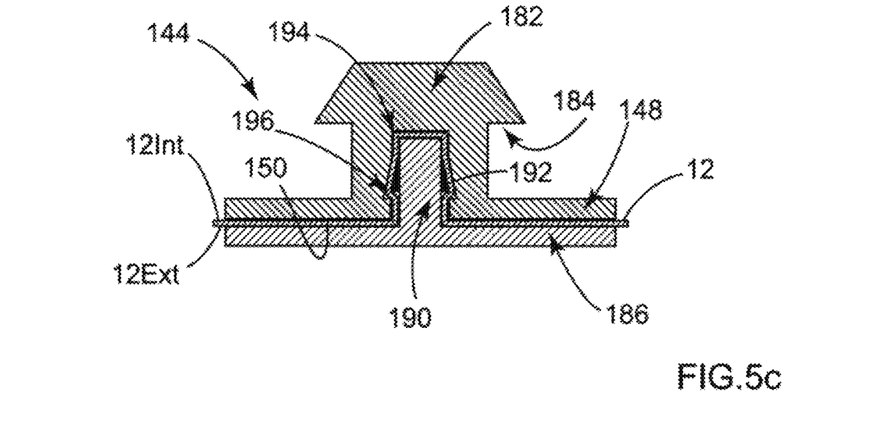
FIG. 5c is a detailed cross-sectional view of a third variant embodiment of a container according to the invention in which, firstly, the peripheral wall has structural continuity, secondly, the attachment member is positioned against the inner face of the peripheral wall, and thirdly, a reciprocal assembly means is positioned against the outer face of the peripheral wall and cooperates with the attachment member so as to hold it in position against the peripheral wall of container.

FIGS. 5a, 5b and 5c represent several variants of the container 10 according to the invention, in which the attachment member 144 and the peripheral wall 20 cooperate differently.

It should first be noted that although these variants are illustrated based on the second embodiment of the guiding element 130, they could be implemented *mutatis mutandis* based on the first embodiment of the guiding element 30.

The variant embodiment in FIG. 5a will be discussed first.

In this variant, the peripheral wall 12 has an attachment opening 12a and the attachment member 144 is welded around this attachment opening 12a, for example on the outer face $12_{EXT}$ of the peripheral wall 12.

This ensures fluid-tightness relative to the exterior, and assembly of the attachment member 144 with the intermediate connection member 170, placed within the inner receiving space 14 of the container 10, remains possible.

The variant embodiment in FIG. 5b will be discussed next.

In this variant, the peripheral wall 12 also has an attachment opening 12a, and the attachment member 144 is composed of a mounting base 148 and a reciprocal assembly means 186.

The reciprocal assembly means 186 is adapted to cooperate with the mounting base 148 in order to fit tightly against the peripheral wall 12 and maintain the attachment member 144 around the peripheral opening 12a. To do this, the reciprocal assembly means 186 is either bonded by an adhesive 188, or is welded as described above (not shown) against the external face $12_{EXT}$ of the peripheral wall 12 which ensures the fluid-tightness of the inner receiving space 14 relative to the exterior of the container 10. Moreover, the mounting base 148 as well as the reciprocal assembly means 186 have complementary geometric profiles which can be mechanically assembled together to hold the mounting base 148 in position against the connection area 146 of the peripheral wall 12.

More particularly, in the current case the reciprocal assembly means 186 has a body 190 extending toward the inner receiving space 14 and provided with a retaining projection 192 having a certain elasticity, while the mounting base 148 has a cavity 194 able to receive the body 190 and provided with a complementary shoulder 196. In this manner, the body 190 of the reciprocal assembly means 186 can be introduced through the attachment opening 12a and into the cavity 194 of the mounting base 148 so that the retaining projection 192 and the complementary shoulder 196 hold the mounting base 148 in position.

This second variant embodiment is advantageous because it allows efficient assembly of the mounting base 148 with the reciprocal assembly means 186, as these two parts can come into direct structural contact with one another. Moreover, given the elasticity of the retaining projection 192, the mounting base 148 is associated with the reciprocal assembly means 186 in a reversible manner. However, this association could also be done in an irreversible manner.

The variant embodiment in FIG. 5c will now be discussed.

This third variant differs from the one in FIG. 5b in that the peripheral wall 12 does not have an attachment opening 12a.

The attachment member 144 is thus composed of a mounting base 148 and a reciprocal assembly means 186 able to cooperate with the mounting base 148 in order to clamp the peripheral wall 12 without impacting its continuity, its structural integrity, and thus its fluid-tightness.

To achieve this, the peripheral wall 12 has a certain flexibility and elasticity, and the reciprocal assembly means 186 is arranged against the external face $12_{EXT}$ of the peripheral wall 12 while the mounting base 148 is arranged against the inner face $12_{INT}$ of this peripheral wall 12. In addition, the mounting base 148 and the reciprocal assembly means 186 have complementary geometric profiles which can be mechanically assembled together to ensure that the mounting base 148 is held in position.

More particularly, the reciprocal assembly means 186 has a body 190 extending toward the inner receiving space 14, provided with a retaining projection 192 having a certain elasticity. As for the mounting base 148, it has a cavity 194 adapted to receive the body 190 without the latter passing through the peripheral wall 12. This cavity 194 is also provided with a complementary shoulder 196 to maintain the retaining projection 192 and therefore the mounting base 148 in position.

This third variant is advantageous because it allows efficient assembly of the mounting base 148 with the reciprocal assembly means 186 without having to pierce the peripheral wall 12 beforehand. In addition, given the elasticity of the retaining projection 192, the mounting base 148 is associated with the reciprocal assembly means 186 in a reversible manner. However, this association may also be done in an irreversible manner.

Figure 6:
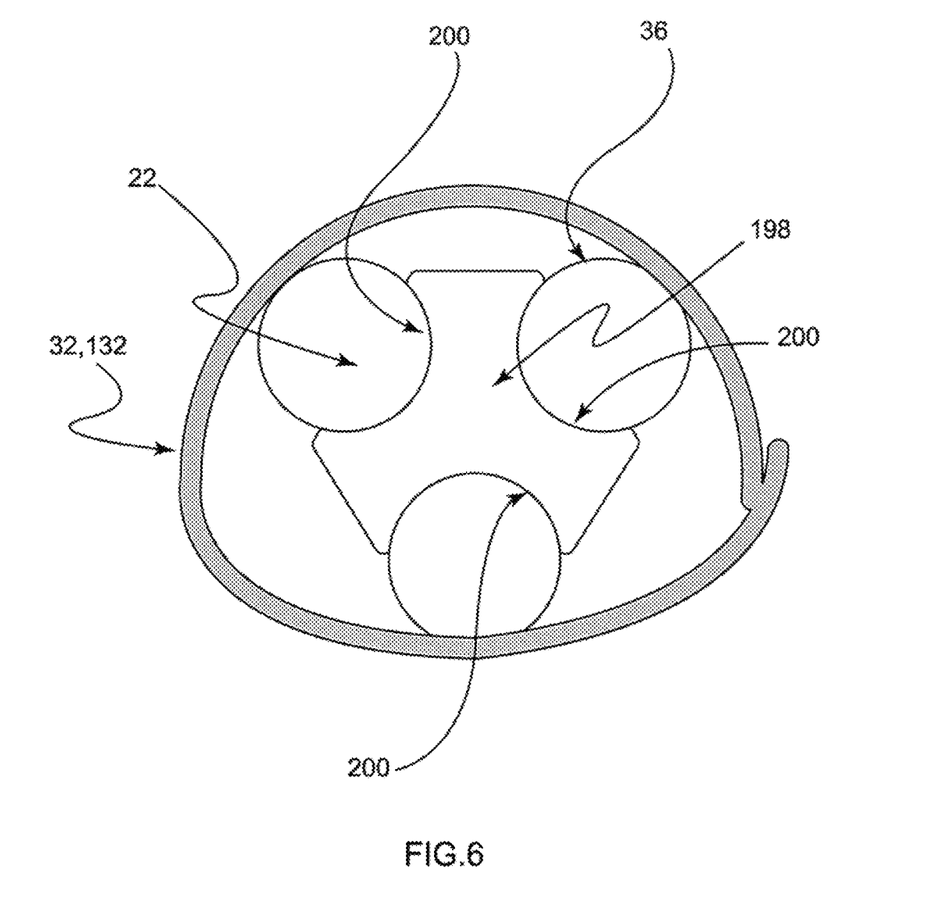
FIG. 6 is a symbolic cross-sectional representation of three transfer pipes held by a gripping member that is part of a container according to the invention in which a spacer has three receiving seats cradling the transfer pipes.

In one embodiment, the container 10 according to the invention also comprises at least one spacer 198 as shown in FIG. 6.

More particularly, this spacer 198 comprises a plurality of receiving seats 200—in this case three—for receiving the transfer pipes 22 and maintaining them in position, preventing said pipes from coming into contact with each other.

These receiving seats 200 are regularly distributed along the periphery of the spacer 198 so that the transfer pipes 22 are subjected to substantially identical clamping forces.

This limits the risk that one of these transfer pipes 22 will be crushed during placement or during use of the gripping member 32, 132.

The method for producing a container 10 according to the invention will now be detailed.

This method comprises a succession of steps consisting, firstly, of having a peripheral wall 12 intended to be closed on itself in order to define an inner receiving chamber 14 capable of receiving the biopharmaceutical content C.

Next, one of the transfer pipes 22 is structurally secured to one of the gripping members 32; 132, and one of the attachment members 44, 144 is attached to any predetermined connection area of the peripheral wall 12 without impacting its fluid-tightness.

According to the invention, after these operations, said gripping member 32; 132 is structurally and functionally assembled with said attachment member 44, 144 in order to form one of the guiding elements which ensures the positioning of the transfer pipe 22 close to said attachment member 44; 144 and therefore close to the connection area 46; 146 to which it is attached.

In the case of a container 10 as described with reference to FIG. 2, the gripping 32 and attachment 44 members are directly and structurally secured to each other.

In the case of a container 10 as described with reference to FIGS. 3, 4a, 4b, and 4c, to ensure the functional assembly of the gripping member 132 with the attachment member 144, it is necessary to structurally secure the intermediate connection member 170 to the gripping member 132 before structurally securing this intermediate connection member 170 to the attachment member 144.

On the other hand, when the container 10 has a set of guiding elements 30; 130 intended to support one or more transfer pipes along a same path, the method according to the invention consists of securing a set of gripping members 32; 132 along the transfer pipe(s) 22. One should also attach a set of attachment members 44; 144 that are structurally distinct and independent of the gripping members 32; 132, to a set of connection areas 46; 146 of the inner face $12_{INT}$ or outer face $12_{EXT}$ of the peripheral wall 12.

Next, each gripping member 32; 132 is then structurally and functionally assembled to the corresponding attachment member 44; 144, in order to guide the transfer pipe(s) 22 close to the peripheral wall 12 and all the way to a location corresponding for example to the area for the introduction or removal of a transfer product 20.

It should be noted that the gripping members 32; 132 can then be secured along the transfer pipe(s) 22 so as to define, between the coupling portions 36; 136, secured intervals of the same length as the connection intervals defined between the connection areas 46; 146. Thus, after the structural or functional assembly of the gripping members 32; 132 and attachment members 44; 144, the transfer pipe(s) 22 define a path coinciding with the path defined by the connection areas 46; 146 on the peripheral wall 12.

Conversely, the gripping members 32; 132 could be secured along the transfer pipe(s) 22 so as to define, between the coupling portions, secured intervals that are different from the connection intervals defined between the connection areas 46; 146. In this manner, after the structural or functional assembly of the gripping members 32; 132 and attachment members 44; 144, the transfer pipe(s) define a path that is different from the path formed by the connection areas 46; 146 on the peripheral wall 12.

Such a variant allows precise definition of the path of the transfer pipe(s) 22, while limiting the number of guiding elements 30; 130 to be used.

The invention claimed is:

1. Container (10) for receiving biopharmaceutical content (C) in liquid, fluid, or gaseous form, comprising:
    a peripheral wall (12) that is closed on itself and that defines an inner receiving chamber (14) able to receive biopharmaceutical content (C);
    at least one transfer pipe (22) having a proximal end portion ($22_{PROX}$) that opens to the inner receiving chamber (14) and a distal end portion ($22_{DIST}$) that opens to the outside of the container (10), to allow carrying a transfer product (20) between said inner receiving chamber (14) and the outside of said container (10);
    at least one guiding element (30; 130) able to be supported by the peripheral wall (12) and to maintain the at least one transfer pipe (22) in position close to said peripheral wall (12) so as to impose a predetermined path between the proximal end portion ($22_{PROX}$) and the distal end portion ($22_{DIST}$);
    wherein the at least one guiding element (30; 130) comprises a gripping member (32; 132) able to be structurally secured to said at least one transfer pipe (22), and an attachment member (44; 144) able to be attached to any predetermined connection area (46; 146) of the peripheral wall (12) without impacting its fluid-tightness;
    characterized in that the gripping member (32; 132) and the attachment member (44; 144) are structurally separate and independent of one another and in that the guiding element (30; 130) has reciprocal assembly means (60; 160) allowing the structural or functional assembly of the gripping member (32; 132), when the latter is secured to the at least one transfer pipe (22), with the attachment member (44, 144), when the latter is attached to the connection area (46; 146), to ensure the positioning of said gripping member (32; 132) close to said attachment member (44, 144) and close to the connection area (46; 146) of the corresponding peripheral wall (12), the reciprocal assembly means (160) comprising an intermediate connection member (170) that is distinct from said gripping member (132) and said attachment member (144).

2. Container (10) according to claim 1, wherein the attachment member (44; 144) has a mounting base (48; 148) provided with sufficient inherent resistance to prevent any structural deformation in the absence of external stresses.

3. Container (10) according to claim 2, wherein the mounting base (48; 148) has a flat face (50; 150) adapted for attachment to one of the connection areas (46; 146) of the peripheral wall (12) by an irreversible attachment method such as welding, gluing, or a similar method.

4. Container (10) according to claim 2, wherein the mounting base (48; 148) and a reciprocal assembly means (186) are adapted to be positioned on each side of the peripheral wall (12) so as to sandwich one of the connection areas (46; 146) of the peripheral wall (12) between them and maintain the attachment member (44; 144) in position on said connection area (46; 146).

5. Container (10) according to claim 4, wherein
    either the mounting base (48; 148) and the reciprocal assembly means (186) have complementary geometric profiles which can be mechanically assembled together, reversibly or irreversibly, without passing through the peripheral wall (12) or altering the structural continuity of said wall;
    or the peripheral wall (12) has at least one attachment opening (12a), with one or the other of the mounting base (48; 148) and the reciprocal assembly means (186) being adapted to be attached around the attachment opening (12a) in a manner that maintains the fluid-tightness of the inner receiving chamber (14) defined by the peripheral wall (12), the other of said mounting base (48; 148) and said reciprocal assembly means (186) being adapted to pass through the attachment opening (12a), the mounting base (48; 148) and the reciprocal assembly means (186) having complementary geometric profiles which can be mechanically assembled together, reversibly or irreversibly.

6. Container (10) according to claim 1, wherein the gripping member (32; 132) is formed by encircling means (34; 134) adapted to grip a coupling portion (36; 136) of the at least one transfer pipe (22).

7. Container (10) according to claim 6, wherein the encircling means (34; 134) have clamping means (40; 140) able to grip the at least one transfer pipe (22) by adjusting to its dimensions, as well as locking means (42; 142) able to lock the clamping means (40; 140) in the clamped position, once the encircling means (34; 134) are adjusted to the dimensions of the at least one transfer pipe (22), without crushing or bending said pipe due to the clamping force;
and/or wherein the encircling means (34; 134) have an elasticity enabling them to clamp the at least one transfer pipe (22) without crushing or bending said pipe due to the clamping force.

8. Container (10) according to claim 1, wherein a portion of the reciprocal assembly means (60) is formed on the gripping member (32), and the complementary portion on the attachment member (44), so as to provide a direct structural mechanical connection between said gripping member (32) and said attachment member (44).

9. Container (10) according to claim 1, wherein the intermediate connection member (170) comprises means (172) for securing to the gripping member (132); and/or
wherein the intermediate connection member (170) has a receiving cradle (175) adapted to match the shape of the coupling portion (136) of the at least one transfer pipe (22) when said pipe is clamped by the gripping member (132).

10. Container (10) according to claim 1, wherein the at least one guiding element (30; 130) is attached to the inner face ($12_{INT}$) or the outer face ($12_{EXT}$) of the peripheral wall (12);
and/or comprising n transfer pipes (22), n being an integer greater than 1, and at least one spacer (198) having m receiving seats (200), m being an integer greater than 1, said seats being adapted to receive the n transfer pipes (22) and prevent said n transfer pipes (22) from coming in contact with each other;
and/or wherein a first guiding element (30; 130) is supported by a first connection area (46; 146) of the peripheral wall (12) and retains the proximal end portion ($22_{PROX}$) of a first transfer pipe (22) so that said pipe is guided to a first location corresponding to the area for the introduction or removal of a first transfer product (20).

11. Method for producing a container (10) for receiving biopharmaceutical content (C) in liquid, fluid, or gaseous foam, according to claim 1, characterized in that it comprises a series of steps consisting of:
having a peripheral wall (12) intended to be closed on itself in order to define an inner receiving chamber (14) capable of receiving biopharmaceutical content (C);
structurally securing at least one transfer pipe (22) having a proximal end portion ($22_{PROX}$) and a distal end portion ($22_{DIST}$), to a gripping member (32; 132);
attaching an attachment member (44; 144) that is structurally separate and independent of the gripping member (32; 132), to any predetermined connection area (46; 146) of the peripheral wall (12) without impacting its fluid-tightness;
then, structurally or functionally assembling said gripping member (32; 132) with said attachment member (44; 144) in order to form a guiding element (30; 130) that ensures the positioning, of said gripping member (32; 132) and of the at least one transfer pipe (22) it secures, close to said attachment member (44; 144) and close to the connection area (46; 146) of the corresponding peripheral wall (12), the reciprocal assembly means (160) comprising an intermediate connection member (170) that is distinct from said gripping member (132) and said attachment member (144).

12. Production method according to claim 11, wherein
either the attachment member (44; 144) has a mounting base (48; 148) provided with a flat face (50; 150) which is attached to one of the connection areas (46; 146) of the peripheral wall (12) by an irreversible attachment method such as welding, gluing, or a similar method;
or the attachment member (44; 144) has a mounting base (148) and a reciprocal assembly means (186) which are positioned on each side of the peripheral wall (12) and are mechanically assembled together, reversibly or irreversibly, without passing through the peripheral wall (12) or altering the structural continuity of said wall, so as to enclose one of the connection areas (46; 146) of the peripheral wall (12) and maintain the attachment member in position on said connection area (46, 146);
or the peripheral wall (12) has at least one attachment opening (12a) and the attachment member (144) has a mounting base (148) and a reciprocal assembly means (186), with one or the other of the mounting base (148) and the reciprocal assembly means (186) being secured around the attachment opening (12a) in a manner that maintains the fluid-tightness of the inner receiving chamber (14) defined by the peripheral wall (12), one or the other of said mounting base (148) and said reciprocal assembly means (186) being positioned so as to pass through the attachment opening (12a), the mounting base (148) and the reciprocal assembly means (186) being mechanically assembled to one another, reversibly or irreversibly, so as to sandwich one of the connection areas (146) of the peripheral wall (12) and hold the attachment member (144) in position on said connection area (146).

13. Production method according to claim 11, wherein the gripping member (32; 132) is structurally secured to the at least one transfer pipe (22) by the grip of encircling means (34, 134) against a coupling portion (36; 136) of said at least one transfer pipe (22);
and/or the gripping member (32; 132) and the attachment member (44; 144) are connected to one another by a direct mechanical connection;
and/or prior to assembly of the gripping member (132) with the attachment member (144), an intermediate connection member (170) that is distinct from said gripping member (132) and from said attachment member (144) is secured to the gripping member (132); said intermediate connection member (170) is then secured to the attachment member (144) to ensure the positioning, of said gripping member (132) and of the at least one transfer pipe (22) it secures, close to said attachment member (144) and close to the connection area (146) of the corresponding peripheral wall (12);
and/or wherein, prior to structurally securing n transfer pipes (22), n being an integer greater than 1, with the gripping member (32; 132), said n transfer pipes (22) are placed in receiving seats (200) formed on a spacer (198) so as to prevent said n transfer pipes (22) from coming in contact with each other and to prevent any of said n transfer pipes (22) from being crushed by the clamping force.

14. Production method according to claim 11, wherein:
a first set of gripping members (32; 132) is secured to a first set of coupling portions (36; 136) arranged along a first set of transfer pipe(s) (22);
a first set of attachment members (44; 144), structurally separate and independent of the gripping members (32; 132), is attached to a first set of connection areas (46; 146) of the peripheral wall (12) without impacting its fluid-tightness; and
then each gripping member (32; 132) of the first set is structurally or functionally assembled to an attachment member (44; 144) of the first set in order to guide the first set of transfer pipe(s) (22) close to the peripheral wall (12) and all the way to a first location corresponding to the area for the introduction or removal of a first transfer product (20).

* * * * *